United States Patent
Brainard et al.

[11] Patent Number: 6,030,391
[45] Date of Patent: Feb. 29, 2000

[54] ALIGNMENT GAUGE FOR METATARSOPHALANGEAL FUSION SURGERY

[75] Inventors: Bradley J. Brainard, Tucson, Ariz.; Mark G. Schrom, White Bear Lake; Thomas E. Brust, Dellwood, both of Minn.

[73] Assignee: Micropure Medical, Inc., White Bear Lake, Minn.

[21] Appl. No.: 09/179,063

[22] Filed: Oct. 26, 1998

[51] Int. Cl.[7] .................................................. A61F 5/00
[52] U.S. Cl. ................................. 606/87; 606/82
[58] Field of Search ..................... 606/87, 79, 56, 606/54, 86, 151, 96, 97, 98; 83/821, 747; 30/286; D24/143

[56] References Cited

U.S. PATENT DOCUMENTS

| | | |
|---|---|---|
| 4,271,836 | 6/1981 | Bacal et al. . |
| 4,502,475 | 3/1985 | Weigle et al. ............................ 128/92 |
| 4,893,619 | 1/1990 | Dale et al. ................................ 606/87 |
| 4,919,119 | 4/1990 | Jonsson et al. . |
| 4,978,347 | 12/1990 | Ilizarov . |
| 5,112,334 | 5/1992 | Alchermes et al. . |
| 5,141,512 | 8/1992 | Farmer et al. . |
| 5,358,504 | 10/1994 | Paley et al. . |
| 5,380,322 | 1/1995 | van den Brink et al. . |
| 5,470,335 | 11/1995 | Du Toit . |
| 5,484,446 | 1/1996 | Burke et al. . |

*Primary Examiner*—Michael Buiz
*Assistant Examiner*—Anthony S. King
*Attorney, Agent, or Firm*—Nikolai, Mersereau & Dietz, P.A.

[57] ABSTRACT

A cutting guide for assuring that mating bone segments will be properly aligned following excision of the joint therebetween comprises first and second alignment bar segments hingedly joined, end-to-end, whose angle of inclination therebetween can be readily set and fixed, is clamped to a toe to be treated by a pair of transversely extending arm members that can be clamped to the metatarsal and phalangeal bones. The coupling between the arm clamped to the metatarsal bone and its associated alignment bar segment allows limited rotation and fixing of the alignment bar. A cutting blade guide member having a blade receiving slot is adjustably mounted to and parallel with the clamping arm affixed to the phalangeal bone. The resulting cuts made through the head of the metatarsal bone and the base of the phalangeal bone on either side of the joint being removed will provide a predetermined inclination and direction to the toe following fusion thereof.

10 Claims, 4 Drawing Sheets

ALIGNMENT GAUGE FOR METATARSOPHALANGEAL FUSION SURGERY

BACKGROUND OF THE INVENTION

I. Field of the Invention

This invention relates generally to surgical equipment, and more particularly to a cutting guide apparatus for use in bone fusion procedures in treating diseased joints.

II. Discussion of the Prior Art

In treating chronic pain associated with arthritic joints in the foot, metatarsophalangeal fusion surgery may be resorted to in which the arthritic joint is excised and the base of the phalangeal bone is fused to that of the metatarsal bone.

It is imperative in carrying out this procedure that the bone cuts made through the head and base portions of the metatarsal and phalangeal bones be at appropriate angles so that when the two bones are brought together and fused, the phalangeal bone will project at an appropriate angle of inclination and direction to assure patient balance and comfort.

The present invention is directed to a surgical alignment gauge which when properly used, will result in bone cuts being made through the heads of the metatarsal and base of the phalangeal bones that assures a predetermined orientation of the bones of the toe following attachment and fusion thereof.

The Alchermes et al. U.S. Pat. No. 5,112,334 describes a surgical instrument for facilitating accurate osteotomy cuts in bone. However, that device is altogether different in its construction and mode of operation from that of the present invention.

Other patents on devices for controlling the angle of cut during orthopaedic surgery include Burke et al. U.S. Pat. No. 5,484,446 and the Du Toit U.S. Pat. No. 5,470,335. Again, the devices described in those patents are altogether different from the alignment gauge comprising the preferred embodiment of the present invention.

SUMMARY OF THE INVENTION

The present invention comprises a surgical cutting gauge or guide for use in orthopaedic surgery, such as on a patient's foot when preforming a metatarsophalangeal fusion procedure. It comprises a first arm member adapted to be clamped to the metatarsal bone of a patient's toe and a second arm member that is adapted to be clamped to the phalangeal bone of that toe. An articulated, dual segment alignment bar is adjustably coupled to the first and second arm members and provision is made to set and fix the two segments at a predetermined angle of inclination and direction corresponding to the desired orientation of the metatarsal and phalangeal bones following the surgery. An elongated cutting guide member is supported by and extends parallel to the second arm member and is adapted to first overlay the head end of the metatarsal bone and later the base end of the phalangeal bone. The elongated cutting guide member includes a longitudinal slot therethrough for receiving a bone-cutting saw blade and maintaining the blade at a pre-established angle of cut assuring that the phalangeal bone will be appropriately oriented relative to the metatarsal bone when the cut ends of each are brought together and fused.

Provision is made in the preferred embodiment for adjusting the location where clamping to the toe bones occurs such that the device can be used with persons having different foot sizes and shapes.

OBJECTS

It is accordingly a principal object of the present invention to provide a new and improved alignment gauge device for use in orthopaedic surgery.

Another object of the invention is to provide an alignment gauge adapted to be removably clamped to adjacent bones whose end portions are to be cut and subsequently fused that establishes an appropriate angle of inclination and direction of the fused toe bone members.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
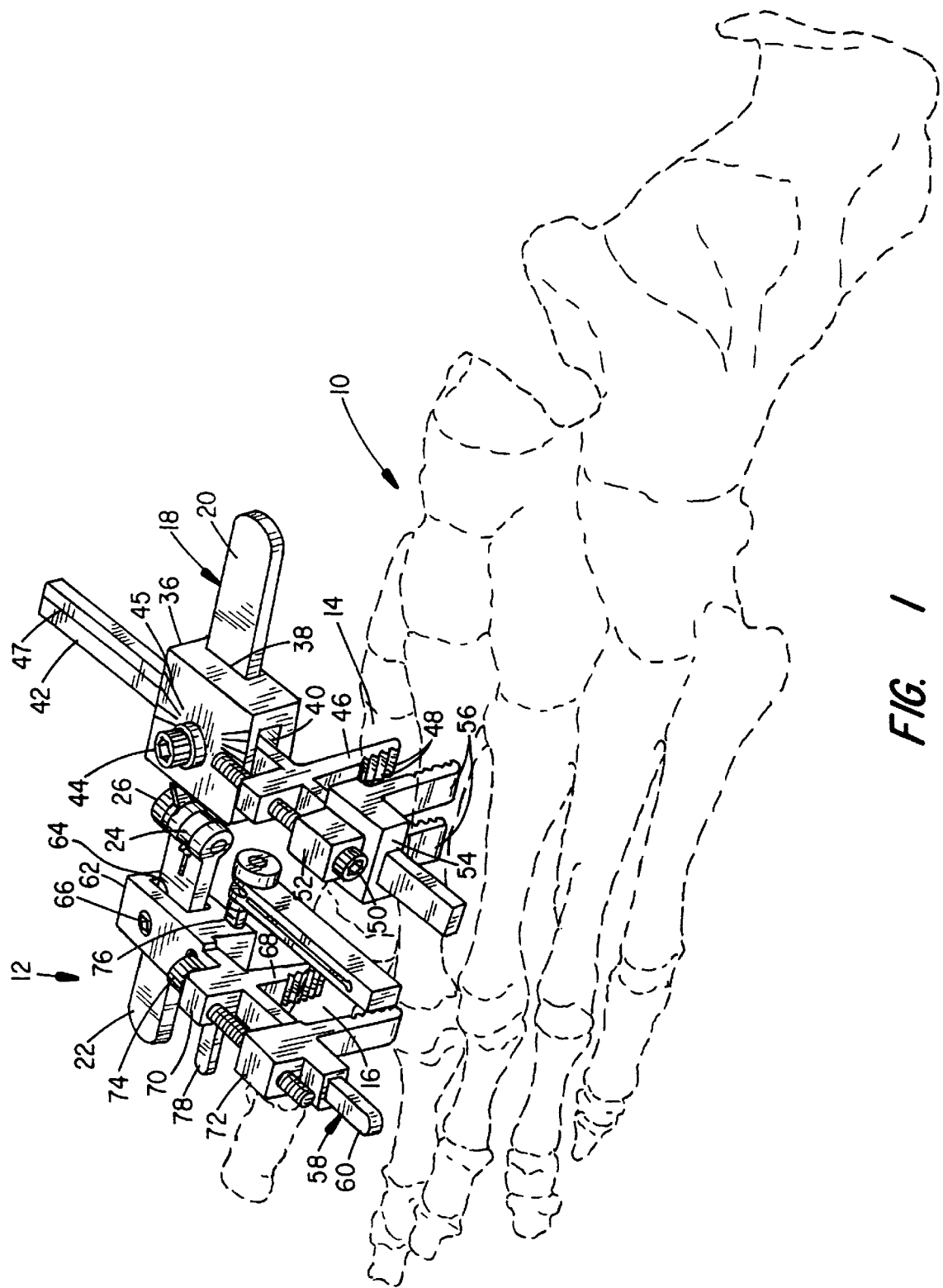
FIG. 1 is a perspective view of the surgical cutting guide of the present invention.

In FIG. 1, there is shown in phantom a skeletal left foot 10 along with a perspective view of the surgical cutting guide of the present invention mounted thereon. The surgical cutting guide is indicated generally by numeral 12. As will be explained in greater detail hereinbelow, in use, the surgical cutting guide 12 is clamped on to the metatarsal bone 14 of the great toe and to the phalangeal bone 16 of that toe.

The surgical cutting guide 12 is seen to comprise an elongated articulated alignment bar 18 comprising a first (metatarsal) and a second (phalangeal) segment 20 and 22, respectively, that are joined in end-to-end relation at a pivot or hinge joint 24. A hinge pin 26 is threaded at one end to engage mating threads in a clevis lug 28 (FIG. 2) so that tightening of the bolt 26 can be used to compress the clevis joint and thereby lock the angle between the metatarsal and phalangeal alignment bar segments 20 and 22.

Figure 4:
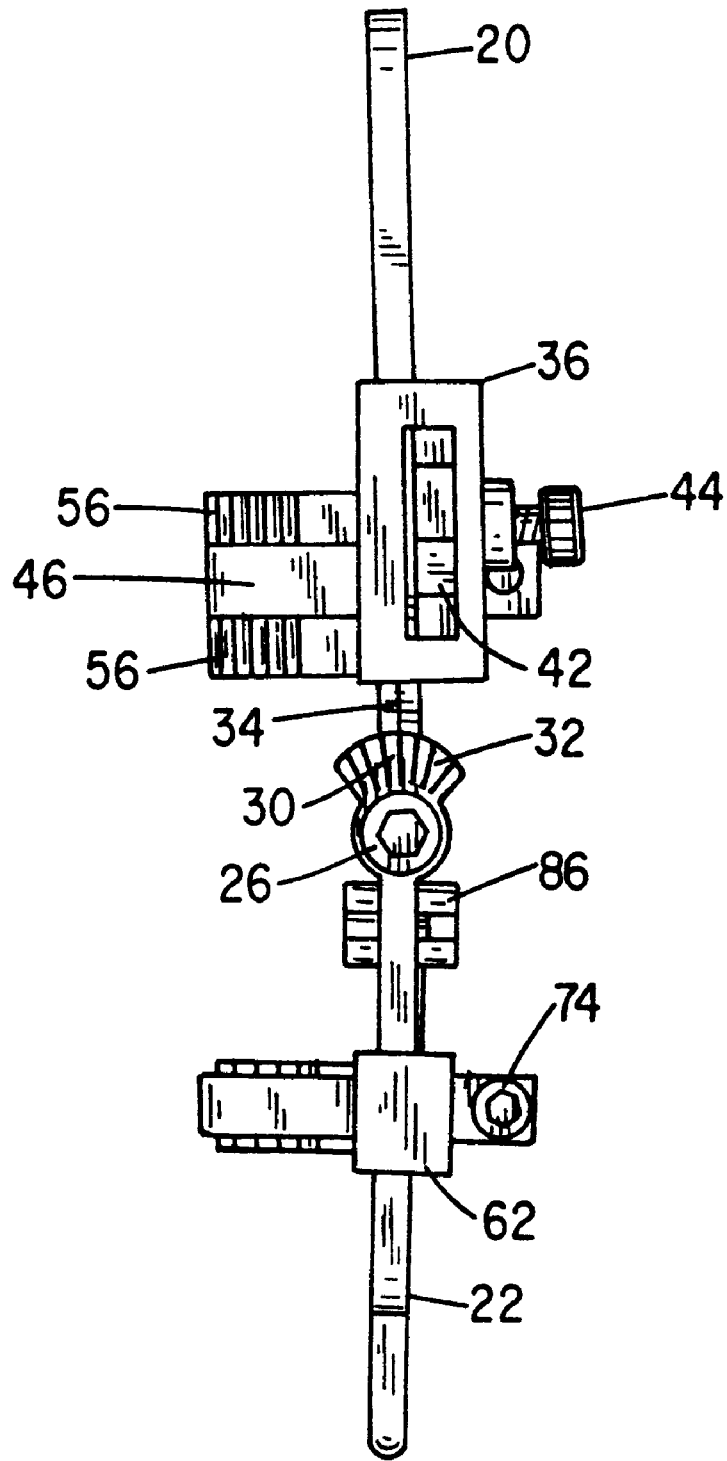
FIG. 4 is a side elevational view thereof.

Referring next to the side view of FIG. 4, an angle plate 30 having radially extending fiducial markings 32 thereon is affixed to the bar segment 22 and cooperates with a mark 34 scribed on the side edge of the bar segment 20 to aid in setting the angle of inclination between the alignment bar segments 20 and 22.

A slide lock base member 36 is provided which has mutually perpendicular guide ways 38 and 40 formed through side walls thereof. The guide way 38 is recessed below the guide way 40. The guide way 38 receives the metatarsal bar segment 20 therethrough while guide way 40 receives a shank portion of a metatarsal arm member 42 therethrough. As can be seen in FIG. 4, the guide way 40 is wider than the width dimension of the metatarsal arm member 42 and, as such, it is possible to rotate the arm 42 within the guide way to a desired angular position before the set screw 44 is tightened down to lock the slide lock base 36 to the bar segment 20 and to also lock the angular position at which the arm 42 is set. To assist in setting such angle, radial degree markings 45 are scribed on the top surface of the slide lock base member 36. A corresponding scribe mark 47 on the shank of member 42 can be aligned with the radial markings 45.

The metatarsal arm 42 includes a stationary clamping member 46 that extends perpendicularly in both directions from the longitudinal axis of the metatarsal arm 42. The lower end portion of clamping member 46 is serrated as at 48 to facilitate gripping of the metatarsal bone 14. The portion of the clamping member 46 projecting upwardly from the metatarsal arm has a threaded bore formed therethrough for receiving the end of a threaded clamping screw 50 therein. The screw 50 passes through a block-like projection 52 of a movable clamping member 54 having downwardly projecting legs 56 that are also serrated to facilitate gripping of the metatarsal bone 14. The clamping member 54 has a rectangular channel formed through its opposed sidewalls, allowing it to slide longitudinally with respect to the metatarsal arm 42. By rotating the clamping screw 50, the legs 56 can be made to move toward the leg 46 to close on and firmly grip the metatarsal bone between the mating jaws of the clamp.

Slidingly received on the phalangeal segment 22 of the alignment bar is a phalangeal arm member 58. It is seen to include an elongated shank portion 60 having a generally rectangular head portion 62 formed on one end thereof. The head portion 62 includes a rectangular bore or channel 64 for receiving the phalangeal alignment bar segment 22 therethrough with a sliding fit. A set screw 66 passes through the head portion 62 to engage the bar segment 22 for locking the phalangeal arm 58 at a desired location there along. The phalangeal arm 58 includes a downwardly depending stationary clamp member 68 and an upwardly projecting flange 70. A movable clamping member 72 is slidingly received on the phalangeal arm 60 and, again, a threaded screw 74 passes through a clearance hole in the flange 70 of the stationary clamping member and through a threaded bore in the movable clamp member 72, such that rotation of the screw 74 allows sliding displacement of the movable clamp member 72 along the shank portion 60 of the phalangeal arm 58. In this fashion, the surgical cutting guide can also be clamped to the phalangeal bone of the toe being prepared for fusion.

Figure 2:
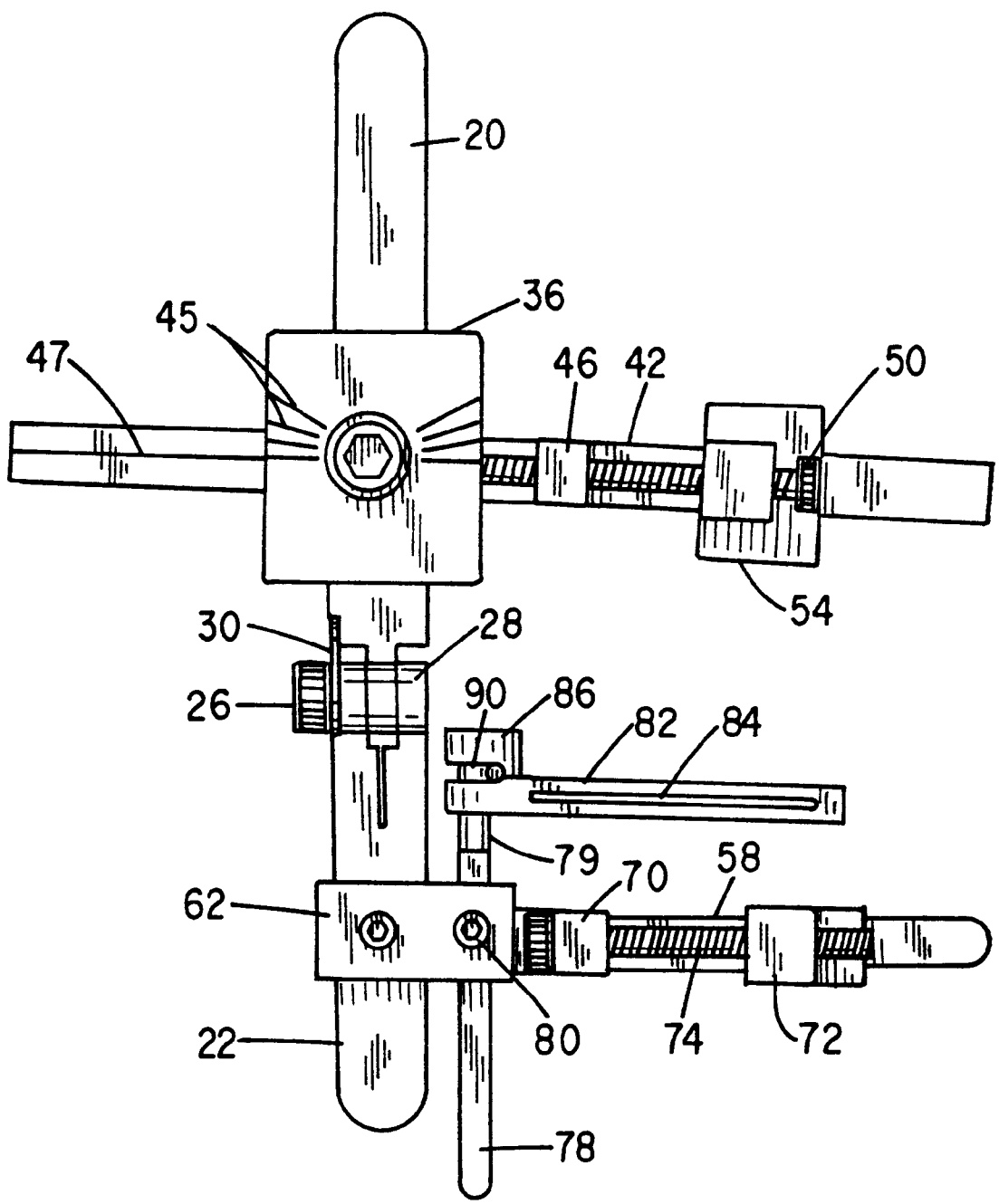
FIG. 2 is a top plan view thereof.
Figure 3:
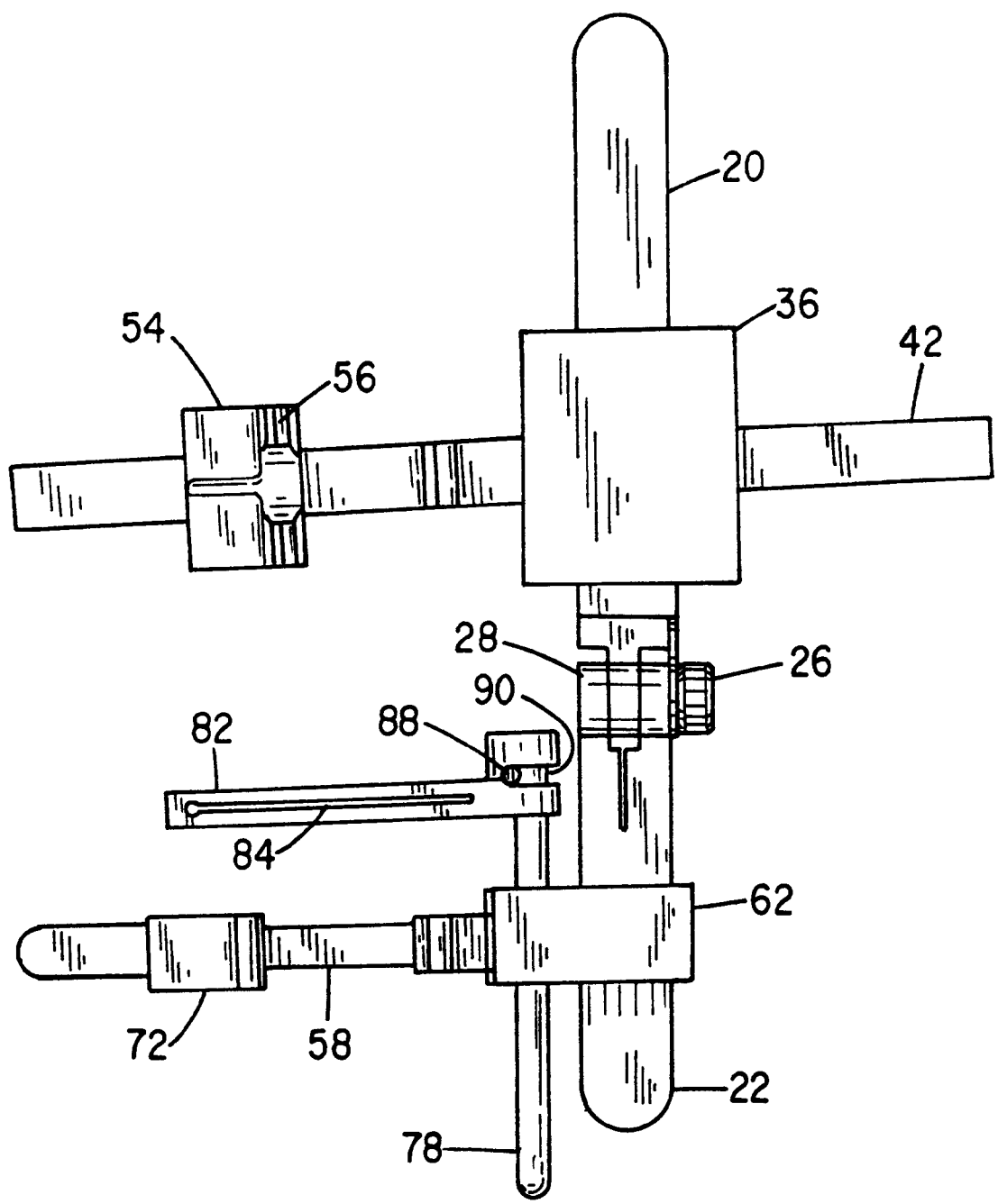
FIG. 3 is a bottom view thereof.

A second semicircular bore or channel 76 is formed through the head portion 62 of the phalangeal arm 58 which extends parallel to the channel 64. This channel receives guide shaft 78 therethrough with a sliding fit and a set screw 80 is provided for locking the pin in position relative to the head portion 62. Rotatably affixed to one end of the pin 78 is a cutting guide member 82. It comprises a bar having a generally rectangular cross section. A longitudinally extending slot 84 is formed through the thickness dimension thereof, the slot 84 being of a width to accept the blade of a bone saw (not shown) therethrough. An integrally formed cylindrical head 86 is provided on the end of the cutting guide member 82 and, as shown in FIG. 2, cooperates with a cylindrical portion 79 of the cutting guide shaft 78 to allow the cutting guide member 82 to swing to a position overlaying a head portion of the metatarsal bone 14 and, later, the base of the phalangeal bone 16 of the patient's toe when the cutting guide assembly 12 of the present invention is clamped in place in the manner previously indicated. A pin 88 (FIG. 3) passing through a radial slot 90 formed in the head member 86 of the cutting guide shaft 78 prevents the cutting guide member 82 from slipping free of the cutting guide shaft 78 while still permitting the desired rotational movement of the cutting guide.

In using the device of the present invention, the orthopaedic surgeon will first employ a scalpel to surgically expose the metatarsal and phalangeal bones 14 and 16 of the toe on either side of the arthritic joint to be fused. The screws 50 and 74 associated with the bone clamping structures will be backed off to open the clamp jaws sufficiently to permit insertion of the metatarsal bone 14 between jaws 48, 56 and the phalangeal bone 16 between the jaws 68 and 72. Once so positioned, the screws 50 and 74 may be tightened using an Allen wrench, causing the clamping jaws to close about and firmly grip the respective toe bones. Using the angle plate 30 as a guide, the phalangeal bar 22 of the alignment bar 18 will be inclined at a desired angle to the metatarsal alignment bar 20. Typically, such angle may be about 15°. It is also important that following fusion, the phalangeal bone of the affected toe be appropriately aligned so that the toe will not be splayed laterally outward, making it difficult to accommodate a shoe or turned inward to the point where the affected toe will rub against and abrade its neighboring toe. To achieve this desired alignment, the metatarsal arm 42 may be pivoted within the slide lock base member 36 until the alignment bar 18 is oriented at a desired angle generally parallel to the toe being repaired.

With the angle of inclination of the phalangeal bone relative to the metatarsal bone and the alignment of the two are appropriately established, the cutting guide member 82 is rotated to overlay the bones of the toe. Now, by loosening the set screw 80 and sliding the cutting guide shaft 78 until the cutting guide 80 overlays the head of the metatarsal bone 14, a bone saw is inserted through the slot 84 in the cutting guide member 80 and is used to saw through the bone. Without moving anything but the cutting guide shaft pin 78 within its guide way 76 in the member 62, the cutting guide member 82 is moved forwardly across the joint to overlay the base portion of the phalangeal bone 16. The set screw 80 is again retightened and the bone saw inserted through the slot 84 in cutting guide 82 to cut through the bone material comprising the base of the phalangeal bone 16. Because of the manner in which the cutting guide of the present invention is used, the bone surfaces following the cutting operation will be at an appropriate angle of inclination and direction so that when brought together and fused using bone screws or the like, the phalangeal bone and metatarsal bone will be appropriately oriented.

While the present invention has been particularly described for use in treating arthritic joints of the great toe on the left foot, those skilled in the art can appreciate that the present invention can be used on the right foot by merely removing the metatarsal arm and the phalangeal arm from their respective alignment bar segment and rotating them by 180° before reconnecting them to the alignment bar segments. The device is adaptable for use with toes other than the great toe.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A surgical cutting guide for use in orthopaedic surgery on a patient's foot, comprising:

(a) an articulated bar having first and second segments hinged together;

(b) a slide lock base member adjustably positionable along the first segment of said articulated bar;

(c) a transversely extending first arm member adjustably positionable in the slide lock base member;

(d) a transversely extending second arm member adjustably positionable along the second segment of the articulated bar;

(e) clamp means on the first arm member adjusted to engage a metatarsal bone of a large toe to the patient;

(f) clamp means on the second arm member adapted to engage a phalangeal bone of said large toe; and (g) a cutting guide member adjustably mounted on the second arm member and including an elongated slot therein adapted to receive a bone cutting instrument therethrough.

2. The surgical cutting guide as in claim 1 wherein the first arm member is pivotally mounted in the slide lock base member and includes fiducial markings for setting an angle between the articulated bar and the first arm member.

3. The surgical cutting guide as in claim 1 and further including:

means for indicating and fixing an angle between the first and second segments of the articulated bar.

4. A surgical cutting guide for use in orthopaedic surgery on a patient's foot, comprising:

(a) a first arm member adapted to be clamped to the metatarsal bone of the patient's toe;

(b) a second arm member adapted to be clamped to the phalangeal bone of said toe;

(c) an articulated alignment bar adjustably coupled to the first and second arm members; and (d) an elongated cutting guide member extending parallel to the second arm member, the cutting guide member adapted to successively overlay the head ends of the metatarsal bone and the base end of the phalangeal bone and having slot therethrough through which a bone cutting saw blade is insertable, the cutting guide member fixing an angle of cut through said bones.

5. The surgical cutting guide as in claim 4 wherein the first arm member is pivotable through a predetermined angle relative to the articulated alignment bar.

6. The surgical cutting guide as in claim 5 wherein the first arm member is adjustably positionable along a length dimension of the articulated alignment bar.

7. The surgical cutting guide as in claim 4 wherein the second arm member is adjustably positionable along a length dimension of the articulated alignment bar.

8. The surgical cutting guide as in claim 7 wherein the articulated adjustment bar includes first and second elongated segments joined end-to-end by a hinge connection, and means for setting and fixing the angle between the first and second elongated segments.

9. The surgical cutting guide as in claim 8 wherein the first arm member is adjustably positionable along the first elongated segment and the second arm member is adjustably positionable along the second elongated segment.

10. The surgical cutting guide as in claim 9 wherein the space between the second arm member and the parallel extending cutting guide member is adjustable.

\* \* \* \* \*